United States Patent [19]

Leonardi-Cattolica et al.

[11] Patent Number: 4,582,991

[45] Date of Patent: Apr. 15, 1986

[54] METHOD OF MEASURING THE DENSITY OF A MATERIAL

[75] Inventors: Anthony M. Leonardi-Cattolica, Houston; Dale H. McMillan, Katy; John D. Jobe, Houston, all of Tex.

[73] Assignee: Shell Oil Company, Houston, Tex.

[21] Appl. No.: 476,952

[22] Filed: Mar. 21, 1983

[51] Int. Cl.$^4$ .................. G01N 9/24; G01N 23/00
[52] U.S. Cl. .................. 250/358.1; 250/391
[58] Field of Search .................. 250/358.1, 390, 391

[56] References Cited

U.S. PATENT DOCUMENTS

| 3,183,351 | 5/1965 | White | 378/89 |
|---|---|---|---|
| 3,246,145 | 4/1966 | Higgins | 250/383 |
| 3,396,272 | 8/1968 | Olson | 378/53 |
| 3,452,202 | 6/1969 | Fedotov et al. | 250/308 |
| 4,039,809 | 8/1977 | Bailey | 250/390 |
| 4,057,729 | 11/1977 | Hewitt | 250/390 |
| 4,277,681 | 7/1981 | Borken | 378/54 |

OTHER PUBLICATIONS

M. K. Nagpal, P. P. Mehta, K. K. Nagpaul and Rama, "Characteristics of a Neutron Moisture Gauge with a Solid State Detector", *Pramana*, (India), vol. 1, No. 2, (1973), pp. 112-116.

H. A. Lepper, Jr. and R. B. Rogers, "Nuclear Methods for Determining the Water Content and Unit Weight of Fresh Concrete", *Journal of Materials*, JMLSA, vol. 6, No. 4, (Dec. 1971), pp. 826-841.

"Audio Signal Announces Interface Arrival", F. L. Resen, The Oil and Gas Journal, Nov. 7, 1955.

*Primary Examiner*—Alfred E. Smith
*Assistant Examiner*—Constantine Hannaher

[57] ABSTRACT

A method of measuring the density of a first material containing a moderator of fast neutrons comprising the steps of: emitting fast neutrons into a sample having a predetermined volume confined in a predetermined shape and sensing the rate of slow neutrons emerging from the sample for each of a plurality of samples of a second material, each of the plurality of samples of the second material having a different known density and neutron moderating and absorbing characteristics that are substantially the same as the neutron moderating and absorbing characteristics of the first material; emitting fast neutrons into a sample of the first material having a predetermined volume confined in a predetermined shape; sensing the rate of slow neutrons emerging from the sample of first material; and comparing the rate sensed in the sensing of the sample of the first material with the rates sensed in the sensing of the plurality of samples of the second material to determine the density of the first material.

20 Claims, 1 Drawing Figure

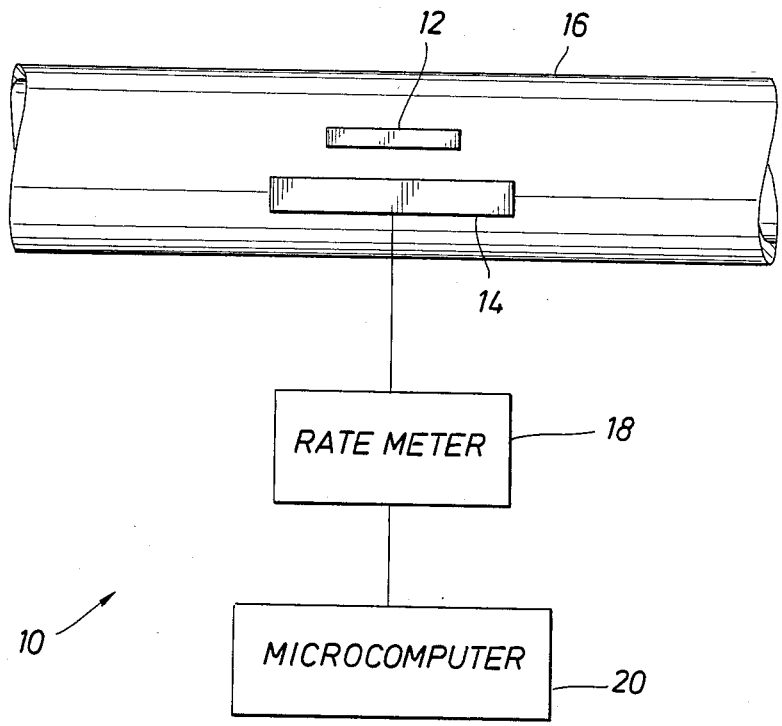

METHOD OF MEASURING THE DENSITY OF A MATERIAL

BACKGROUND OF THE INVENTION

This invention relates to a method of measuring the density of a material containing a moderator of fast neutrons, such as hydrogen. It is intended that the term "material" as used herein includes gases, liquids and solids.

SUMMARY OF THE INVENTION

In accordance with the present invention there is provided a method of measuring the density of a material containing a moderator of fast neutrons, for example, hydrogen. Fast neutrons are emitted into a plurality of calibration samples of the material to be monitored or a material having substantially the same neutron moderating and absorbing characteristics as the monitored material. Each of these calibration samples has a predetermined volume confined in a predetermined shape and a different known density. The rate of slow neutrons emerging from each of the calibration samples in response to the emitted fast neutrons is sensed. Fast neutrons are then emitted into a sample of the material to be monitored; this sample has a predetermined volume confined in a predetermined shape and an unknown density. The rate of slow neutrons emerging from the sample of monitored material is sensed, and the density thereof is determined by comparing the rate of slow neutrons detected in the sensing of the monitored material with the rates of slow neutrons detected in the sensing of the calibration samples.

Alternatively, a functional relationship between the rates of slow neutrons detected in the sensing of the calibration samples and their densities is determined. This functional relationship is used to modify the rate of slow neutrons detected in the sensing of the monitored material to determine its density. Preferably, the calibration samples and the monitored material are tested in the same container; however, different containers can be used provided that they are substantially the same size and shape, are made of materials that have substantially the same neutron moderating and absorbing characteristics and are located in surroundings that have substantially the same neutron moderating effects. If different containers are used, preferably, the same source and detector are located in substantially the same positions on the respective containers. However, separate sources and detectors can be used if the sources are the same type and have neutron emission rates that are substantially the same and the detectors are the same type and have substantially the same sensitivities.

The method of the present invention employs a fast neutron source, such as californium-252, a slow neutron detector that is insensitive to the fast neutrons, such as a helium-3 detector, a rate meter and storage means. The neutron source and neutron detector are positioned on the exterior of the container which can be, for example, a test cell or pipe. Predetermined volumes of the calibration samples are individually positioned in the container. The output of the rate meter is a signal proportional to the neutron detection rate of the neutron detector. The rates of neutrons sensed from the calibration samples are then stored, for example, in a microcomputer so that the neutron detection rate for the monitored material during normal operations can be compared with the correlated data in the microcomputer to determine its density.

The system of the present invention can be used to monitor numerous processes. For example, in a process in which materials which contain no hydrogen are blended with hydrogen bearing polymers to produce a fire retardant product, the detector count rate is a measure of the density of the product and, hence, a measure of the composition of the product. The system would provide the compositional information required for continuous blending of the fire retardant and polymer. In another application, the system of the present invention could be used to monitor the degree of conversion of reactants to products in the product stream of a chemical reactor, where the reactants and products of the chemical reaction have different densities but the elemental composition of the reactants plus products is not changed by the reaction. Still further, the system of the present invention can be employed to meter gas in a pipeline if the linear velocity of the gas is known. Other objectives, advantages and applications of the present invention will be made apparent by the following detailed description of the preferred embodiments of the present invention.

BRIEF DESCRIPTION OF THE DRAWING

The FIGURE is a schematic block diagram of a densimeter according to the present invention.

DETAILED DESCRIPTION OF THE PREFERRED EMBODIMENTS

Referring to the FIGURE, one embodiment of the densimetric system of the present invention is indicated generally by numeral 10. It should be noted that the backscatter embodiment disclosed in the Figure is served by way of illustration and not limitation, since other configurations can be employed, such as where the source and detector are located on opposite sides of the container. System 10 has a fast neutron source 12 and a slow neutron detector 14 positioned proximate to one another on pipe 16. Fast neutron source 12 can be, for example, californium-252, and slow neutron detector 14 can be, for example, a helium-3 neutron detector. Detector 14 is connected to rate meter 18 which provides an output signal proportional to the rate of neutrons detected by detector 14, and rate meter 18 is connected to microcomputer 20.

A plurality of calibration samples of different known densities of the material to be monitored by system 10 are passed through pipe 16 so that the neutron detection rate can be determined for each sample. If desired, samples of other materials can be substituted for the samples of the monitored material, provided that the neutron moderating and absorbing characteristics of the monitored material and the substituted materials are substantially the same. For example, if the monitored material contains hydrogen, then other hydrogen containing materials can be used during the calibration runs. Preferably, the actual density and the respective neutron detection rate provided by rate meter 18 for each calibration run are stored in microcomputer 20 so that when the monitored material is moving through pipe 16 under normal operations the output from rate meter 18 can be compared with the neutron detection rates for the calibration samples to determine its density. Alternatively, a functional relationship between the densities of the calibration samples and the neutron detection rates associated therewith can be determined. This functional relationship is applied by microcomputer 20 to the neutron detection rate provided by rate meter 18 during normal monitoring operations to obtain the density of the material moving through pipe 16.

It should be noted that system 10, as shown in the FIGURE, has incorporated microcomputer 10 to compare or modify the output of rate meter 18 to obtain the actual density of the material flowing through pipe 16; however, the plurality of neutron detection rates related to the plurality of calibration samples can be recorded in a table or graph for use by an operator to determine the density of the material flowing through pipe 16. Alternatively, the operator can be provided with the functional relationship determined from analyzing the neutron rate measurements of the calibration samples, or conventional multiplier circuitry can be employed to apply the functional relationship to the output of rate meter 18. In addition, it should be noted that, although the FIGURE discloses the use of system 10 on pipe 16, any test cell or container can be employed to provide a predetermined volume of the material to be tested. Different test containers can be used during calibration and normal monitoring, if the containers have substantially the same size and shape, are made of materials that have substantially the same neutron moderating and absorbing characteristics and are located in surroundings that have substantially the same neutron moderating effects. If different containers are used, preferably, the same source and detector are located in substantially the same positions on the respective containers. However, separate sources and detectors can be used if the sources are the same type and have neutron emission rates that are substantially the same and the detectors are the same type and have substantially the same sensitivities.

It is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. A method of measuring the density of a first material containing a moderator of fast neutrons, said method comprising the steps of: emitting fast neutrons at a predetermined rate into a sample having a predetermined volume confined in a predetermined shape and sensing as a function of said predetermined rate of emitting fast neutrons into said sample the rate of slow neutrons emerging from said sample for each of a plurality of samples of a second material, each of the plurality of samples of said second material having a different known density and neutron moderating and absorbing characteristics that are substantially the same as the neutron moderating and absorbing characteristics of said first material; emitting fast neutrons at said predetermined rate into a sample of said first material having a predetermined volume confined in a predetermined shape; sensing as a function of said predetermined rate of emitting fast neutrons into said sample the rate of slow neutrons emerging from said sample of first material; and comparing the rate sensed in the sensing of the sample of said first material with the rates sensed in the sensing of the plurality of samples of said second material to determine the density of said first material.

2. A method as recited in claim 1, wherein said steps of emitting fast neutrons into a sample and sensing the rate of slow neutrons emerging from the sample for each of a plurality of samples of a second material comprises the steps of emitting fast neutrons into a sample and sensing the slow neutrons emerging therefrom for a plurality of samples of a plurality of different second materials with each of the plurality of samples comprising only one of the plurality of different second materials and each of said plurality of different second materials having neutron moderating and absorbing characteristics that are substantially the same as the neutron moderating and absorbing characteristics of said first material.

3. A method as recited in claim 2, wherein said step of emitting fast neutrons into a sample of first material comprises placing the sample of first material in a first container, and said step of emitting fast neutrons into a sample for each of a plurality of samples of a second material comprises placing each of the plurality of samples of second material separately in a second container, said first and second containers having substantially the same shape and neutron moderating and absorbing characteristics.

4. A method as recited in claim 3, wherein said moderator of fast neutrons comprises hydrogen.

5. A method as recited in claim 1, wherein said steps of emitting fast neutrons into a sample and sensing the rate of slow neutrons emerging from the sample for each of a plurality of samples of a second material comprises the steps of emitting fast neutrons into a sample and sensing the slow neutrons emerging therefrom for a plurality of samples of said first material with each of the plurality of samples of said first material having a different known density.

6. A method as recited in claim 5, wherein said step of emitting fast neutrons into a sample of first material comprises placing the sample of first material in a first container, and said step of emitting fast neutrons into a sample for each of a plurality of samples of a second material comprises placing each of the plurality of samples of second material separately in a second container, said first and second containers having substantially the same shape and neutron moderating and absorbing characteristics.

7. A method as recited in claim 6, wherein said moderator of fast neutrons comprises hydrogen.

8. A method as recited in claim 1, wherein said step of emitting fast neutrons into a sample of first material comprises placing the sample of first material in a first container, and said step of emitting fast neutrons into a sample for each of a plurality of samples of a second material comprises placing each of the plurality of samples of second material separately in a second container, said first and second containers having substantially the same shape and neutron moderating and absorbing characteristics.

9. A method as recited in claim 8, wherein said step of emitting fast neutrons into a sample for each of a plurality of samples of a second material comprises placing each of the plurality of samples of second material separately in a third container, and said step of emitting fast neutrons into a sample of first material comprises placing the sample of first material in said third container.

10. A method as recited in claim 1, wherein said moderator of fast neutrons comprises hydrogen.

11. A method of measuring the density of a first material containing a moderator of fast neutrons, said method comprising the steps of: emitting fast neutrons at a predetermined rate into a sample having a predetermined volume confined in a predetermined shape and sensing as a function of said predetermined rate of emitting fast neutrons into said sample the rate of slow neutrons emerging from said sample for each of a plurality of samples of a second material, each of the plurality of samples of said second material having a different known density and neutron moderating and absorbing characteristics that are substantially the same as the neutron moderating and absorbing characteristics of said first material; determining a functional relationship between the rates of slow neutrons sensed and the densities of the plurality of samples of said second material; emitting fast neutrons at said predetermined rate into a sample of said first material having a predetermined volume confined in a predetermined shape; sensing as a function of said predetermined rate of emitting fast neutrons into said sample the rate of slow neutrons emerging from said sample of first material; modifying the rate of slow neutrons sensed in said sensing of the sample of said first material by said functional relationship to determine the density of said first material.

12. A method as recited in claim 11, wherein said steps of emitting fast neutrons into a sample and sensing the rate of slow neutrons emerging from the sample for each of a plurality of samples of a second material comprises the steps of emitting fast neutrons into a sample and sensing the slow neutrons emerging therefrom for a plurality of samples of a plurality of different second materials with each of the plurality of samples comprising only one of the plurality of different second materials and each of said plurality of different second materials having neutron moderating and absorbing characteristics that are substantially the same as the neutron moderating and absorbing characteristics of said first material.

13. A method as recited in claim 12, wherein said step of emitting fast neutrons into a sample of first material comprises placing the sample of first material in a first container, and said step of emitting fast neutrons into a sample for each of a plurality of samples of a second material comprises placing each of the plurality of samples of second material separately in a second container, said first and second containers having substantially the same shape and neutron moderating and absorbing characteristics.

14. A method as recited in claim 13, wherein said moderator of fast neutrons comprises hydrogen.

15. A method as recited in claim 11, wherein steps of emitting fast neutrons into a sample and sensing the rate of slow neutrons emerging from the sample for each of a plurality of samples of a second material comprises the steps of emitting fast neutrons into a sample and sensing the slow neutrons emerging therefrom for a plurality of samples of said first material with each of the plurality of samples of said first material having a different known density.

16. A method as recited in claim 15, wherein said step of emitting fast neutrons into a sample of first material comprises placing the sample of first material in a first container, and said step of emitting fast neutrons into a sample for each of a plurality of samples of a second material comprises placing each of the plurality of samples of second material separately in a second container, said first and second containers having substantially the same shape and neutron moderating and absorbing characteristics.

17. A method as recited in claim 16, wherein said moderator of fast neutrons comprises hydrogen.

18. A method as recited in claim 11, wherein said step of emitting fast neutrons into a sample of first material comprises placing the sample of first material in a first container, and said step of emitting fast neutrons into a sample for each of a plurality of samples of a second material comprises placing each of the plurality of samples of second material separately in a second container, said first and second containers having substantially the same shape and neutron moderating and absorbing characteristics.

19. A method as recited in claim 18, wherein said step of emitting fast neutrons into a sample for each of a plurality of samples of a second material comprises placing each of the plurality of samples of second material separately in a third container, and said step of emitting fast neutrons into a sample of first material comprises placing the sample of first material in said third container.

20. A method as recited in claim 11, wherein said moderator of fast neutrons comprises hydrogen.

* * * * *